United States Patent [19]

Bowen et al.

[11] 3,952,092

[45] Apr. 20, 1976

[54] ORAL PREPARATIONS

[76] Inventors: William Henry Bowen, 50 Hillcrest Road, Purley, Surrey; Sidney Alan Barker, 1 Abdon Ave., Selly Oak, Birmingham, both of England

[22] Filed: June 7, 1973

[21] Appl. No.: 367,892

[30] Foreign Application Priority Data

June 9, 1972 United Kingdom............... 27048/72

[52] U.S. Cl..................................... 424/50; 424/52
[51] Int. Cl.² ...................... A61K 7/28; A61K 7/18
[58] Field of Search........................... 424/85, 49–58

[56] References Cited
UNITED STATES PATENTS 3,538,230  11/1970  Pader et al............................ 424/50

FOREIGN PATENTS OR APPLICATIONS 1,617,886  1/1971  Germany............................... 424/85

OTHER PUBLICATIONS

Schick et al., *J. Biological Chem.*, Vol. 236, pp. 2477–2485, 1961.

*Primary Examiner*—Richard L. Huff
*Attorney, Agent, or Firm*—Hill, Gross, Simpson, Van Santen, Steadman, Chiara & Simpson

[57] ABSTRACT

The present invention provides a composition which comprises at least one agglutinin which is a site-directed homing agent attached to a biologically active molecule which is effective in modifying the nature of a target site. There is also provided a process for the production of a composition which comprises attaching at least one agglutinin which is a site-directed homing agent to a biologically active molecule which is effective in modifying the nature of a target site.

10 Claims, No Drawings

ORAL PREPARATIONS

The present invention relates to a composition comprising a biologically active molecule. More particularly it relates to combatting those effects of microorganisms which contribute to the development of mouth diseases especially dental caries and periodontal disease.

The preparations of the present invention are designed to act at sites where dental plaque accumulates on tooth surfaces. It is well known that dental plaque affords a site for bacterial colonization and that the metabolic activities of such bacteria contribute to the volume of plaque and to the deleterious effects exerted on teeth and their surrounding soft tissues. For example, the ability of certin bacteria to synthesize extracellular polysaccharide from sugar assimilated in the diet, adds to the bulk and adhesiveness of the plaque and thereby provides an environment in which bacteria and their fermentation products can be sheltered from the self-cleansing action of mouth fluids or masticatory friction.

Additionally the dental plaque that forms on the teeth and along the gum margin causes inflammation. Such inflammation leads to gum recession and conditions generically known as periodontal disease.

Polyglucans are especially important examples of such extracellular products of bacteria and were found in all plaques examined by Critchley, Wood, Saxton and Leach (Caries Research 1, 1967, 122). The formation and structure of dental plaque has been discussed by many workers. When a tooth erupts it is now accepted that it is covered by a cuticle which is believed to be the final product of the ameloblasts (Winkler and Backer Dirks, International Dental Journal 8, 1958, 561). A secondary cuticle forms rapidly, is relatively free from bacteria, and contains both protein and carbohydrate. This is believed to arise from denatured salivary glycoproteins. Deposition of plaque matrix follows and bacteria generally represent some 70% of the total volume of plaque. Inorganic compounds based on elements such as calcium and phosphorus also play an important part in the structure of the plaque.

Dental plaque is not susceptible to removal by conventional oral hygiene practices such as toothbrushing or mouth rinsing because it is located in inaccessible regions such as the interproximal areas of adjacent teeth, as well as pits and fissures on enamel surfaces, and because it is adherent to the tooth enamel. Dentists can remove plaque by careful scraping with sharp instruments and with the aid of disclosing solutions which make these deposits more easily detected. The present invention seeks to obviate this expensive and timeconsuming procedure by making available a medicinal preparation which can be used by individuals.

Attempts have been made to prevent or to reduce plaque formation by using an enzyme such as dextranase either in the form of a food additive or in a therapeutic agent such as dentifrice or mouthwash. Experiments in animals (Bowen, W. H., British Dent. Journal, Vol. 131, 1971, page 445) have shown that by the addition of dextranase to sugar, caries incidence and plaque formation can be reduced. However, there are disadvantages in using dextranase as a food additive, for example, its inactivation by heat in the course of food preparation and the difficulty of achieving sufficient concentration of the enzyme at the site of polysaccharide synthesis.

According to the present invention there is provided a composition comprising at least one agglutinin attached to a biologically active molecule. The agglutinin is utilised as a site-directed homing agent and the biologically active molecule is effective in modifying the nature of a target site.

A particular embodiment of the present invention provides an oral medicinal preparation comprising at least one agglutinin attached to an anti-plaque or anti-caries substance. The present invention provides for the protection of teeth and/or surrounding soft tissues by providing a preparation comprising at least one agglutinin attached to an anti-plaque or anti-caries substance in contact with the tooth and/or surrounding soft tissue surface.

One embodiment of the present invention relates to the modification of enzymes such as dextranase, by attaching them to an agent that has a binding capacity for a component of the dental plaque, thus providing an enzyme preparation which is adsorbed onto the dental plaque so that it can perform such useful functions in oral hygiene as breaking down or inhibiting the formation of such polysaccharides as dextran or other polysaccharides which contribute to plaque formation and thus to deleterious effects described hereinabove.

Whilst the present invention is particularly described with reference to the use of dextranase as the biologically active molecule, it is not restricted thereto. The biologically active molecule may be, for example, an enzyme catalyst an antibiotic, a protein complexed with fluoride, any other antiplaque or anti-caries molecule or any combination thereof. Other enzymes which may be used include levanase, enzymes that can assist in the oral digestion of food such as $\alpha$-amylase and glucamylase which act on starch and dextrin components of food, lysozyme (muramidase) which is known to be present in human saliva, and substances of the anti-lactobacillus system (as described by Bowen, W. H. on page 487 of Biology of the Periodontium edited by A. H. Melcher and W. H. Bowen, Academic Press, 1969). Such enzymes can be used singly or in combination with one another. This is particularly true of mixtures of dextranase and amylase. Other anti-plaque or anti-caries substances which may be used include fluorides, calcium glycerophosphate, antibiotics and dextran sucrase inhibitors.

The present invention can provide a preparation of enzymes coupled to agents that bind to polysaccharides or carbohydrate moieties of glycoproteins in dental plaque. Such agents can be isolated from plant, animal, and human sources and are found in the group of substances called specific agglutinins which include protectins, lectins (G. I. Pardoe, C. Uhlenbruck and U. Reifenberg, Medical Laboratory Technology, 28, (1971) 255) and antibodies.

A particular useful lectin is concanavalin. Antibodies which may be used include $\gamma$-globulin, described more particularly in Example 1 hereinbelow.

The agglutinin functions as a homing agent in guiding its enzyme attachment to the appropriate part of the dental plaque. The mode of attachment of the agglutinin to the enzyme must be such that both the binding capacity of the agglutinin for its target and the catalytic activity of the enzyme to which it is attached are substantially retained. No single method can be expected to be universally applicable but in practice the following methods have been found to have great utility in the coupling procedure. These involve the use of toluene 2:4 diisocyanate to couple antibodies to dextranase. The method of using toluene 2:4 diisocyanate is based on the method of Schick and Singer (J. Biol Chem. 236 (1961) 2477) the difference being the use of carbonate buffer instead of borate for the second stage. The antibody component of monkey serum has also been attached to dextranase using glutardialdehyde at pH 5.0 and 37°C as well as by the use of diazosulphanilic acid at 0°C +pH 6.0.

Concanavalin A has been coupled to dextranase using glutardialdehyde at 25°C and a pH of 5.0, by using diazosulphanilic acid at 0°C and a pH of 6.0 and by the use of the diazonium salt of O-dianisidine in pH 7.0 buffer containing 0.15M KCl. In particular the glutardialdehyde method has been found effective with several different sources of dextranase of widely differing specific activity.

The fact that the components of the concanavalin A-dextranase conjugate each retained their individual biological activity was unexpected since both concanavalin A and dextranase are known to have an affinity for dextran and the binding capacity of the former could well have inhibited the enzymic activity of the latter. In fact there appears to be a definite lag phase before the full enzymic activity of the dextranase is exhibited.

The enzyme preparations of the present invention will find uses when incorporated into mouth washes either as a single enzyme-agglutinin conjugate or as mixtures of enzyme-agglutinin conjugates since it has been demonstrated that they attach themselves to dental plaque. Thus, when a human subject had rinsed his mouth with concanavalin-dextranase conjugate, a sample of his plaque was taken and treated with fluorescently labelled anti-concanavalin serum. Patches of clear fluorescence could be seen and photographed.

The enzyme-agglutinin preparations of the present invention will also find uses when incorporated into tooth paste either as a single enzyme-agglutinin conjugate or as a mixture of enzyme-agglutinin conjugates. The remaining components of the tooth paste will be such that (a) they will not compete in complexing with the enzyme-agglutinin conjugate, (b) they will not inactivate or suppress the enzymic activity of the enzyme-agglutinin conjugate.

The enzyme-agglutinin or other biologically active molecule-agglutinin conjugates of the present invention can be incorporated in carriers such as chewing gum, lozenges or chewable tablets, or even in a food or beverage. The carrier could be a material which could be incorporated into the plaque and which releases the conjugate slowly with time.

In the following Examples, Examples 1 to 4 illustrate how γ-globulin can be conjugated to the lectin concanavalin; Examples 5 to 10 illustrate how the enzyme dextranase may be conjugated to the lectin concanavalin Examples 11 and 12 show conjugation of various antibiotics to concanavolin and Example 13 describes an experiment with a composition of the present invention. However, the present invention is by no means limited to these Examples since it includes the analogous conjugation of other biologically active substances to other homing agents of the agglutinin type; thus providing a means for their attachment to the plaque in therapeutic concentration.

Examples 11 and 12 show that antibiotics can be attached to Concanavalin with retention of much of their biological activity. Two methods have been used to attach the antibiotic to the concanavalin. The first involves the use of glutardialdehyde as above and the second involves the separate thiolation of the two components (lectin and antibiotic) followed by an oxidation step to joint the thiol groups together from the separate molecules of thiolated lectin and thilated antibiotic in the form of a disulphide bridge. The thiolation can be carried out in aqueous solution under very mild conditions using N-acetyl cysteine thiolactone or N-acetyl homo-cysteine thiolactone. The former can thilate within a wider range of pH than the latter and therefore, where required under milder conditions appropriate to the stabilities of the lectin and antibiotic. Although more time consuming than the glutardialdehyde method, the thiolation/oxidation procedure has the special merits of (1) only introducing non-toxic amino acids into the lectin-antibiotic complex; (2) enabling the junction between lectin and antibiotic to be varied according to the pH and thilating agent employed (thus N-acetyl cysteine thiolactone can react with hydroxyl groups at slightly acidic pH, with phenol groups after a much longer time at that pH and amino groups at an alkaline pH and since the separate components are thilated, this ensures that those skilled in the art have the requisite flexibility to find the optimum conditions for retention of antibiotic or lectin activity as these are varied); (3) providing a junction, namely -S-S-, which, though stable in aqueous solutions containing air, would be susceptible to reduction to the separate thiols by enzymes in the bacteria of the dental plaque (this would, under these circumstances, provide a slow release formulation where it is required). This method can be used to join lectins to enzymes since both the former and the latter always possess some groups of the required type outlined above. Methods are therefore provided for the implementation of the invention to a wide variety of agents that "home" on dental plaque namely certain agglutinins, lectins and antibodies and to effect their junction to a variety of antiplaque substances. The literature contains evidence that by the use of different types of enzymes and proteins the nature of the antiplaque substance can be extended to include fluoride and other substances. Thus fluoride complexes with serum albumin (di San Stefano, Brunese and Gombes, Arch. Stomatol., 7 287 (1966); Rugyiero, Brunese, Gombers and di San Stefano, Arch. Stomatol, 8 177 (1967)).

Certain metal-containing proteins such as perioxidase (Dunford and Alberty, Biochemistry, 6, 447 (1967)), carboxypeptidase-Mg, and catalase (Brill, Sandberg, Biophys., J. 8, 669 (1968)) can coordinate fluoride ions.

EXAMPLE 1

Formation of a Dextranase Antibody conjugate using Toluene 2:4 Diisocyanate

The antibody used in Examples 1 to 4 was γ-globulin from antiserum carried in monkeys inoculated against cariogenic streptococci. This was obtained from the antiserum using DEAE 52 cellulose (Whatman Ltd.) by the method of Stanworth et al (Nature, 188, 156 (1960)).

The experiment was carried out according to the method of Schick and Singer (J. Biol. Chem. 2477, 236 (1961)) with modifications.

Dextranase 2 mgs. (1 mg/cm$^3$ in 0.1M Phosphate buffer pH7.5) was treated with 10 ml Toluene 2:4 Diisocyanate. The mixture was stirred magnetically at 0°C for 25 mins. The mixture was then centrifuged at 0°C for 30 mins and the supernatant was carefully removed from the unreacted diisocyanate. The supernatant was then allowed to stand for an additional hour at 0°C.

This solution was then mixed with a solution of antibody-I$^{125}$ 2 mgs (1 mg/cm$^3$ in Carbonate buffer pH9.5 0.1M) at 37°C (i.e. antibody labelled with I$^{125}$).

After standing at 37°C for an hour the solution was passed down a Biogel P10 column (16cm × 1.5cm) and 1cm$^3$ fractions were collected.

The optical densities of the fractions at 280nm were read on a Unicam SP500 Spectrophotometer. The fractions with high optical density were then pooled and dialysed versus Phosphate buffer 0.1M ph7.0.

EXAMPLE 2

Formation of a Dextranase-Antibody Conjugate using Diazosulphanilic Acid

Sodium nitrite was dissolved in 0.5 N hydrochloric acid (12 mg/cm$^3$) at 0°C. Sulphanilic acid was dissolved in water (20mg/cm$^3$) and cooled to 5°C. Equal volumes of the two solutions were then mixed taking care that the temperature did not rise above 5°C during mixing or afterwards. The so-prepared diazosulphanilic acid was then adjusted to pH 6.0 using sodium acetate and used immediately as follows:-

Dextranase (2 mgs) (1 mg/cm$^3$ in Phosphate 0.1M ph6.0) and antibody labelled with I$^{125}$ (2 mgs) (1 mg/cm$^3$ in Phosphate 0.1M ph6.0) were mixed together and cooled to 0°C in ice. 50ml of Diazosulphanilic acid prepared as described above was then added and the mixture was left to stand at 0°C for 1 hour. The solution was then applied to a column of Biogel P10 (16cm × 1.5cm) and 1cm$^3$ fractions collected. These were scanned at 280nm and the high optical density fractions with high molecular weight were pooled and stored at 0°C.

EXAMPLE 3

Formation of a Dextranase-Antibody conjugate using Glutardialdehyde

Dextranase 2mgs (1 mg/cm$^3$ in Citrate buffer pH5.0,0.1M) and antibody labelled with I$^{125}$ 2mgs (1mg/1cm$^3$ in citrate buffer pH5.0,0.1M) were mixed at room temperature (21°C) and 100ml of glutardialdehyde (25% in H$_2$O) were added. The mixture was stirred for 1 hour at 37°C. The reaction mixture was then applied to a column of Biogel P10 (16 × 1.5cm) and 1cm$^3$ fractions collected. The fractions were scanned for protein at 280nm and the protein containing fractions were pooled.

EXAMPLE 4

Evidence for the Formation of Dextranase-Antibody conjugates

The protein containing fractions from each of Examples 1 to 3 were applied to a column of Biogel P300 (16 × 1.5cms) which had been previously calibrated with free dextranase-antibody. Fractions (1cm$^3$) were collected and tested for dextranase activity and also antibody protein which was detected by its I$^{125}$ label. In each case a high molecular weight compound was detected containing both dextranase activity and also antibody protein.

Cellulose acetate electrophoresis on the products of Examples 2 and 3 was also carried out on the free proteins and the high molecular weight fractions from the Biogel P300 column. In each case a low mobility band was detected in the reaction mixture which was not present in the free proteins.

EXAMPLE 5

Formation of a Dextranase-Concanavalin A conjugate using Diazosulphanilic Acid

Dextranase 2mgs (1mg/cm$^3$ in Phosphate buffer pH6.0,0.1M) and Concanavalin A 2mgs (1mg/cm$^3$ in Phosphate buffer pH6.0,0.1M) were mixed together at 0°C and 50ml of freshly prepared Diazosulphanilic acid was added. The mixture was allowed to stand for 1 hour at 0°C.

The reaction mixture was then applied to a column of Biogel P10 (18 × 1.5cm) to remove excess coupling reagent. Fractions were collected (1cm$^3$) and scanned for protein at 280nm. The protein containing fractions were then pooled.

EXAMPLE 6

Formation of a Dextranase-Concanavalin A conjugate using Glutardialdehyde

Dextranase 2mgs (1mg/cm$^3$ in Citrate buffer ph5.0,0.1M) and Concanavalin 2mgs (1mg/cm$^3$ in Citrate buffer pH5.0,0.1M) were mixed together at room temperature (21°C). 100ml of glutardialdehyde (25% in H$_2$O) was added and the mixture was incubated at 37°C for 1 hour.

The reaction mixture was then applied to a Biogel P10 column (18 × 1.5cms) to remove excess coupling reagent. Fractions were collected (1cm$^3$) and scanned for protein at 280nm. The protein containing fractions were then pooled.

EXAMPLE 7

Formation of a Dextranase-Concanavalin A conjugate using the Diazonium salt of o-Dianisidine Dextranase 2mgs (1mg/cm$^3$ in Phosphate buffer pH7.0,0.1M) and Concanavalin A 2mgs (1mg/cm$^3$ in Phosphate buffer ph7.0,0.1M) were mixed together at room temperature. 300ml of a freshly prepared solution of the diazonium salt of o-dianisidine in 0.15 M potassium chloride solution were than added and the solution was stirred for 1 hour at room temperature (21°C).

The reaction mixture was then applied to a column of Biogel P10 (20 × 1.5cms). Fractions (1cm$^3$) were collected and scanned at 280nm for protein. The protein containing fractions were then pooled.

EXAMPLE 8

Evidence for the formation of Dextranase-Concanavalin A conjugates in Examples 5 to 7

The protein containing fractions from Examples 5 to 7 were all applied to Biogel P300 columns (16 × 1.5cms) which had previously been calibrated with both free Dextranase + Concanavalin A. In each case the fractions collected (1cm$^3$), were examined for both Dextranase activity, and Concanavalin A binding properties and they were indeed found to be present in a high molecular weight product.

Further evidence for the formation of a high molecular weight compound in the case of the glutardialdehyde linked conjugate containing both Dextranase and Concanavalin A (Example 6) can be seen from the following Examples 9 and 10.

EXAMPLE 9

Precipitation of the conjugate with Glycogen and measurement of the decrease in Dextranase activity of the supernatant A 1cm$^3$ sample of conjugate of Example 6 was taken and mixed with 400mg of glycogen (1 mg/cm$^3$ solution in phosphate buffer pH7.2) and was incubated at 37°C for 4 hours. At the same time an identical control was performed using 400ml of buffer instead of glycogen solution.

After incubation 50ml of a saturated sodium chloride solution was added to aid precipitation and the reaction mixtures were left over night (16 hours). The solutions were then centrifuged and the Dextranase activity in the supernatants measured.

It was found that the glycogen treated sample contained 33% of the original dextranase activity in the supernatant.

Since an identical experiment using a mixture of free Dextranase and Concanavalin A with an identical protein concentration, resulted in no decrease in Dextranase activity compared with the relevant control this suggests that a chemically linked Dextranase-Concanavalin A conjugate has indeed been formed.

EXAMPLE 10

Alteration of Reaction profile of Action of Dextranase on Dextran

200ml of Dextranase-Concanavalin A conjugate of Example 6 was incubated at 37°C with 2.5cm$^3$ of 0.5% Dextran solution (citrate buffer 0.2M pH5.0). Aliquots were taken at 0,10,20 and 30 minutes and the quantity of reducing sugar produced was measured.

At the same time, an identical experiment was carried out using 200 ml of Dextranase-Concanavalin A mixture of identical concentration which had not been treated with coupling reagent as in Example 6.

From the plots of reducing sugar produced versus time it was seen that in the case of the conjugate there was a definite time lag before full enzymic activity was attained which was not present in the mixture.

This is further evidence that a chemically linked complex of Dextranase and Concanavalin A was obtained.

EXAMPLE 11

The formation of conjugates of concanavalin A with various antibiotics by coupling with glutaraldehyde (i) Formation of a vancomycin-concanavalin A conjugate using glutaraldehyde Concanavalin A 5 mgs (1mg/cm$^3$ in acetate buffer pH 5.0; 0.1M) and vancomycin 5mgs (1mg/cm$^3$ in acetate buffer pH 6.0; 0.1M) were mixed and glutaraldehyde (259 in H$_2$O; 125 μl) was added and the mixture incubated at 21°C for 1 hour. The reaction mixture was then applied to a column of Biogel P10 (18 × 1.5 cm) which had been pre-calibrated with both vancomycin and concanavalin A. Fractions (2cm$^3$) were collected.

The product appeared as a single high molecular weight peak (Fractions 7-12) containing concanavalin A activity with elimination of the low molecular weight peak due to vancomycin which was eluted in fractions 44-58 in the calibration.

The molecular weight material was then tested for biological activity with the following results compared with native vancomycin.

| Organism | Quantity required for inhibition of growth | |
|---|---|---|
| | Vancomycin HCl | Conjugate* |
| Escherichia coli | 62.5 μ g/cm$^3$ | INACTIVE |
| Streptococcus faecalis | 1.9 μ g/cm$^3$ | 20 μ g/cm$^3$ |
| Staphylococcus aureus | 0.4 μ g/cm$^3$ | 5 μ g/cm$^3$ |
| Pseudomonas aeruginosa | INACTIVE | INACTIVE |

*Figures corrected for concanavalin A contribution to weight used.

(ii) Formation of an ampicillin-concanavalin A conjugate using glutaraldehyde

Concanavalin A 5mgs (1mg/cm$^3$ in acetate buffer pH 5.0; 0.1M) and ampicillin 5 mgs (1mg/cm$^3$ in acetate buffer pH 5.0; 0.1M) were mixed and glutaraldehyde (25% in H$_2$O; 125 μl) added. The reaction mixture was allowed to stand at room temperature (21°C) for 1 hour.

The mixture was then eluted on a pre-calibrated Biogel P 60 column and fractions (2cm$^3$) collected. These were then assayed for both concanavalin A and ampicillin activity.

The results revealed that ampicillin was no longer present in a detectable form at the elution volume of native ampicillin (fractions 28–38) indication that coupling had indeed taken place with formation of a conjugate containing concanavalin A activity which was eluted in fractions 18-28.

This high molecular weight product was then tested for biological activity with the following results compared with native ampicillin:

| Organism | Quantity required for inhibition of growth | |
|---|---|---|
| | Ampicillin | conjugate* |
| Escherichia coli | 0.4 μ g/cm$^3$ | 31.7 μ g/cm$^3$ |
| Streptococcus faecalis | 1.9 μ g/cm$^3$ | 15.6 μ g/cm$^3$ |
| Staphylococcus aureus | 0.2 μ g/cm$^3$ | 3.9 μ g/cm$^3$ |
| Pseudomonas aeruginosa | INACTIVE | INACTIVE |

*Figures corrected for concanavalin A contribution to weight used.

EXAMPLE 12

The formation of conjugates of concanavalin A with various antibiotics by oxidation of thiolated derivatives of antibiotics and concanavalin A (i) Formation of a bacitracin-concanavalin A conjugate using N-actyl homocysteine thiolactone (a) Thiolation of concanavalin A and bacitracin Concanavalin A 10 mgs (2mg/cm$^3$ in oxygen free carbonate buffer pH 10.6; 0.1M) was treated with N-acetyl homocysteine thiolactone (20mg/cm$^3$ in oxygen free distilled water, 50 μl) at 0°C for 2 hours. The reaction was then stopped by the addition of oxygen free phosphate buffer (0.1M; ph 7.0) until the pH of the reaction mixture was 7.0.

The reaction mixture was then eluted on a Biogel P10 column (16 × 1.5 cm³) with oxygen free phosphate buffer (pH 7.0; 0.1M) and fractions (2cm³) were collected. The fractions were scanned at 280nm and assayed for concanavalin A activity and thiol content. The high molecular weight fractions (7–11) exhibiting all of these properties were then stored under nitrogen at 0°C.

A sample of bacitracin was then treated in the same way and eluted from a Biogel P10 column (18 × 1.5 cm). The fractions in this case were scanned for protein at 280nm and thiol content and the high molecular weight fractions (7–11) exhibiting both properties were stored under nitrogen at 0°C.

Thiolated bacitracin was found to contain 0.8 SH residues per molecule of bacitracin while thiolated concanavalin A contained 36 SH residues per molecule. (b). Coupling of thiolated bacitracin to thiolated concanavalin A.

Thiolated concanavalin A 5 mgs (1mg/cm³ in oxygen free phosphate buffer pH 7.0; 0.1M) and thiolated bactracin 5mgs (0.7 mg/cm³ in oxygen free phosphate buffer pH 7.0; 0.1M) were mixed together and left to stand exposed to the atmosphere. Aliquots (500µl) were removed at intervals and tested for free thiol content. After standing for 36 hours no free thiol groups could be detected in the reaction mixture. The reaction mixture was then eluted on a pre-calibrated Biogel P150 column (18 × 2cms) and fractions (2cm³) were collected.

The fractions were scanned for protein at 280nm and concanavalin A activity and were found to contain a single high molecular weight peak (fractions 12–20) exhibiting both of these properties. There was, however, no longer a peak due to thiolated bacitracin (calibration position fractions 40–52) which indicated that the bacitracin and active concanavalin A were both contained in the high molecular weight product from the reaction.

The high molecular weight product was then tested for biological activity compared with native bacitracin and its thiolated form with the following results:

| Organism | Quantity required for inhibition (µg/cm³) | | |
|---|---|---|---|
| | Bacitracin | Bacitracin Thiol | Conjugate* |
| Escherichia coli | 250 | INACTIVE | INACTIVE |
| Streptococcus faecalis | 31.2 | 12.5 | 50 |
| Staphylococcus aureus | 7.8 | 12.5 | 12.5 |
| Pseudomonas aeruginosa | INACTIVE | INACTIVE | INACTIVE |

*Quantity corrected to allow for weight of concanavalin A in conjugate (ii) Formation of an erythromycin-concanavalin A conjugate The concanavalin A employed was thiolated by the N-acetyl homocysteine thiolactone method described above.

Erythromycin was thiolated using N-acetylcysteine thiolactone by the following method.

N-acetylcysteine (1g) was dissolved in dioxane (dry 15 ml). Dicyclohexyl carbodiimide (1.2 g) was added. The reaction was left to stir for 12 hours, filtered and evaporated (1.10 g).

200 mg N-acetylcysteine thiolactone was dissolved in dioxane (15 ml) and erythromycin (1.0 g) added. The solution was stirred at room temperature over night, evaporated at room temperature in vacuo leaving a colourless residue. This was dissolved in chloroform (20 ml), washed with water (3 × 5 cm³) dried and evaporated giving a pale white crystalline product (II) m.p, 128°–130°.

Thiolated concanavalin A 5mgs (1mg/cm³ in oxygen-free phosphate buffer pH 7.0; 0.1M) was mixed with N-acetylcysteine erythromycin thiol 10 mgs (2 mg/cm³ in oxygen free phosphate buffer pH 7.0; 0.1M). The mixture was left exposed to the atmosphere, aliquots (500 µl) being removed at intervals and tested for the presence of thiol groups. After 36 hours no free thiol groups were detected. The reaction mixture was then applied to a pre-calibrated column of Biogel P10 (16 × 1.5 cm) and eluted with phosphate buffer (0.1M; pH 7.0). Fractions (2cm³) were collected and scanned for protein at 250nm and tested for concanavalin A activity. A high molecular weight fraction exhibiting these characteristics was found (Fractions 7-12). The elution volume of this fraction corresponded to that of inactive concanavalin A in the calibration experiment.

This high molecular weight fraction was then tested for biological activity compared with that exhibited by native erythromycin (I) and N-acetylcysteine erythromycin thiolactone (II).

| Organism | Quantity required of inactivation (µ g/cm³) | | |
|---|---|---|---|
| | I | II | Conjugate* |
| Escherichia coli | 1.9 | 62.5 | 50 |
| Streptococcus faecalis | 0.4 | 7.8 | 6.25 |
| Staphylococcus aureus | 0.03 | 0.4 | 0.8 |
| Pseudomonas aeruginosa | 15.6 | INACTIVE | INACTIVE |

*Corrected for concanavalin A contribution to weight used.

Evidence for the formation of concanavalin A-antibiotic conjugates in the above Example 12

(i) Precipitation of the conjugates with Glycogen and measurement of the decrease in antibiotic activity of the supernatent.

(a) Concanavalin A-Ampicillin

An 8 cm³ sample of conjugate was taken and mixed with 500 µl of glycogen solution (4% in 1M sodium chloride in phosphate buffer pH 7.2, 0.1M) and was left to stand at 21°C for 4 hours. At the same time an identical control was performed using 500 µl of buffer instead of glycogen solution.

At the same time a mixture of concanavalin A and ampicillin of identical concentration was also treated with 500 µl of the glycogen solution for 4 hours.

The solutions were then centrifuged and the supernatents tested for biological activity with the following results:

| Organism | Quantity required for inhibition (µ g/cm³) | | |
|---|---|---|---|
| | Conjugate Untreated | Conjugate Treated | Mixture |
| Escherishia coli | 6.2 | (12.5) 25 | 1.6 |
| Streptococcus faecalis | (0.8) 3.1 | (12.5) 25 | (0.8) 3.1 |
| Staphylococcus aureus | (0.4) 1.6 | 1.6 | 0.2 |
| Pseudomonas | INACTIVE | INACTIVE | INACTIVE |

-continued

| Organism | Quantity required for inhibition ($\mu$ g/cm³) | | |
|---|---|---|---|
| | Conjugate Untreated | Conjugate Treated | Mixture |
| aeruginosa | | | |

Figures in parenthesis indicate commencement of inhibition. Absence of these figures indicates that inhibition was clearly defined at the concentrations stated.

EXAMPLE 13 These results indicate that the precipitation of the conjugate resulted in a decrease in antibiotic activity compared with the controls indicated that a chemically linked concanavalin A-ampicillin conjugate had indeed been formed.

Groups of Wistar rats were given drinking water containing the following preparations:
a. a mixture of dextranase and concanavalin;
b. dextranase;
c. concanavalin;
d. a conjugate of concanavalin and dextranse prepared as in example 6.

All the animals received Stephan diet 580 ad libitum. The experiment ran for 21 days. The results and the number of rats used as shown below.

| | Number of animals | Number of Carious Lesions |
|---|---|---|
| a) Dextranase and Concanavalin | 14 | 5.2 |
| b) Dextranase | 14 | 4.9 |
| c) Concanavalin | 13 | 4.7 |
| d) Conjugate | 13 | 3.2 |

We claim:
1. A method of inhibiting dental caries which comprises applying to the teeth a composition comprising an anti-caries effective amount of an anticaries agent bound to a lectin.
2. A method as claimed in claim 1 in which the attachment is effected with a compound selected from the group consisting of glutardialdehyde, tolune 2:4-diisocyanate, diazotised o-dianisidine, glutaraldehyde and diazosulphanilic acid.
3. A method as claimed in Claim 1, wherein said anti-caries agent is selected from the group consisting of vancomycin, ampicillin, bacitracin and erythromycin.
4. A method as claimed in claim 1 in which lectin is attached to dextranase.
5. The method as claimed in Claim 1, wherein said anti-caries agent comprises enzymes.
6. The method as claimed in Claim 1, wherein said anti-caries agent comprises antibiotics.
7. The method as claimed in Claim 1, wherein said anti-caries agent comprises proteins complexed with fluoride.
8. A method as claimed in Claim 1, wherein said lectin is concanavalin.
9. A method as claimed in claim 8 in which concanavalin is attached to a biologically active molecule selected from vancomycin, ampicillin, bacitracin and erythromycin.
10. A method of inhibiting dental caries which comprises applying to the teeth a composition comprising an anti-caries amount of dextranase bound to concanavalin.

* * * * *